United States Patent [19]

Parr

[11] Patent Number: 5,735,905
[45] Date of Patent: Apr. 7, 1998

[54] SHOCK ABSORBING ELEMENT FOR A LOAD BEARING PROSTHESIS

[75] Inventor: Charles H. Parr, San Antonio, Tex.

[73] Assignee: Southwest Research Institute, San Antonio, Tex.

[21] Appl. No.: 651,445

[22] Filed: May 22, 1996

Related U.S. Application Data

[63] Continuation of Ser. No. 430,195, Apr. 27, 1995, abandoned.

[51] Int. Cl.$^6$ ............................................. A61F 2/36
[52] U.S. Cl. ................................................. 623/23; 623/18
[58] Field of Search ............................. 623/16, 18, 22, 623/23, 49

[56] References Cited

U.S. PATENT DOCUMENTS

| | | |
|---|---|---|
| 3,707,006 | 12/1972 | Bokros et al. . |
| 3,938,198 | 2/1976 | Kahn et al. . |
| 4,314,381 | 2/1982 | Koeneman . |
| 4,892,551 | 1/1990 | Haber . |
| 4,908,034 | 3/1990 | Weightman et al. ............ 623/23 |
| 5,158,570 | 10/1992 | Schey et al. .................... 623/49 |
| 5,181,929 | 1/1993 | Prats et al. ...................... 623/23 |
| 5,201,881 | 4/1993 | Evans ............................... 623/20 |
| 5,336,267 | 8/1994 | Kubein-Meesenburg et al. ...... 623/23 |
| 5,389,107 | 2/1995 | Nassar et al. ................... 623/23 |
| 5,593,445 | 1/1997 | Waits ............................... 623/22 |

OTHER PUBLICATIONS

Robert H. Finney, et al. "Design of Elastomeric Components by using the Finite Element Technique." *The Shock and Vibration Bulletin*, 47:1 (Sep. 1977) 177–188.

P.B. Lindley, "Engineering Design with Natural Rubbers." *NR Technical Bulletin5*, (1970) 1–50.

*Primary Examiner*—John G. Weiss
*Assistant Examiner*—Bruce E. Snow
*Attorney, Agent, or Firm*—Madan & Morris, PLLC

[57] ABSTRACT

The present invention provides a method and structure for absorbing shock in a load bearing prosthesis, particularly in a load-bearing skeletal prosthesis. Where the prosthesis is a hip-joint replacement, the invention provides a method and structure for absorbing shock (1) at the interface between the femoral head and cup, and (2) at the interface between the femur and the stem of the prosthesis. Where the prosthesis is a femoral head prosthesis, the prosthesis is formed using two separate components which are mechanically connected using an elastomeric component. The connection permits relative motion between the structural components of the prosthesis, with the elastomeric component acting as a passive shock absorbing element.

10 Claims, 3 Drawing Sheets

SHOCK ABSORBING ELEMENT FOR A LOAD BEARING PROSTHESIS

This application is a continuation of application Ser. No. 08/430,195 filed on Apr. 27, 1995 now abandoned.

FIELD OF THE INVENTION

The present invention relates to shock absorption in load bearing medical implants, such as the femoral head of a hip-joint prosthesis.

BACKGROUND OF THE INVENTION

In recent years, surgical techniques have been developed for the replacement of damaged or diseased joints, amputations, resections for malignancy or disease, and various types of malformation. Complete or partial replacement of the coxo-femoral or hip joint is one of the most common operations in this area, particularly among the elderly or in patients having severe arthritic conditions.

In early procedures, hip joint surgery was limited to repair or replacement of the femoral head, typically using an autologous bone graft. A disadvantage of this procedure was that it required the surgeon to open a second surgical site in order to remove healthy bone and replace the damaged skeletal member(s). Another disadvantage was that the surgeon had to sculpt the healthy bone into the desired configuration during the limited time period of the operation. To overcome these disadvantages, prosthetic devices were developed as an alternative to the use of healthy bone for attachments, reinforcements, or replacements to hip joints and various other skeletal members.

The primary goals for any prosthetic device are compatibility, or avoiding a toxic reaction or rejection by the patient's immune system, and effective simulation of the relevant body member over an extended period of time. When a prosthesis will be subjected to high stresses during use, other goals become important as well. For a load bearing skeletal member, like a hip joint, the adjacent bone must be able to endure stresses and carry loads as if the natural hip joint had not been removed.

A hip joint prosthesis typically consists of (1) a one-piece femoral head, consisting of a stem and a ball or head, and (2) a separate socket, or acetabulum, in which the ball articulates. Typical hip joint prostheses are subject to failure at two interfaces. One is the interface between the patient's femur and the stem of the prosthetic femoral head. Another is the interface between the ball of the femoral head and the socket, or acetabulum.

The failure mechanisms are complex, but the loads imposed by normal activities such as walking, running, and dancing, are a major contributing factor. The impact from the foregoing activities is imparted from the feet through the legs, the hip joints, the pelvis, and the spine. In each section of the body, the natural viscosity of the body tissues tends to dampen the loads so that the impact overloads progressively decrease as they flow through the body from the feet to the head.

When a hip joint or another load bearing member is replaced, much of the adjacent, naturally viscous body tissue is removed or degenerates. In order for a load bearing prosthesis to successfully replace the natural load bearing member, the impact load upon a load bearing prosthesis must be reduced. Where the load bearing prosthesis is a hip-joint prosthesis, the stress on the acetabular cup also must be reduced.

Apparently, the high localized load imposed upon bone by hard surfaced prosthetic material pinches off fine blood vessels and crushes adjacent tissue, causing bone resorption and necrotic degeneration in the affected zone. The resorption and degeneration often is noted only after the patient is partially rehabilitated and attempts to use the affected limb or member in a normal, vigorous manner. Efforts to prevent such bone resorption and necrotic degeneration have been unavailing.

SUMMARY OF THE INVENTION

The present invention provides a method and structure for absorbing shock in a load bearing prosthesis, particularly in a load-bearing skeletal prosthesis. Where the prosthesis is a hip-joint replacement, the invention provides a method and structure for absorbing shock (1) at the interface between the femoral head and cup, and (2) at the interface between the femur and the stem of the prosthesis. Where the prosthesis is a femoral head prosthesis, the prosthesis is formed using two separate components which are mechanically connected using an elastomeric component. The connection permits relative motion between the structural components of the prosthesis, with the elastomeric component acting as a passive shock absorbing element.

DETAILED DESCRIPTION OF THE INVENTION

Figure 1:
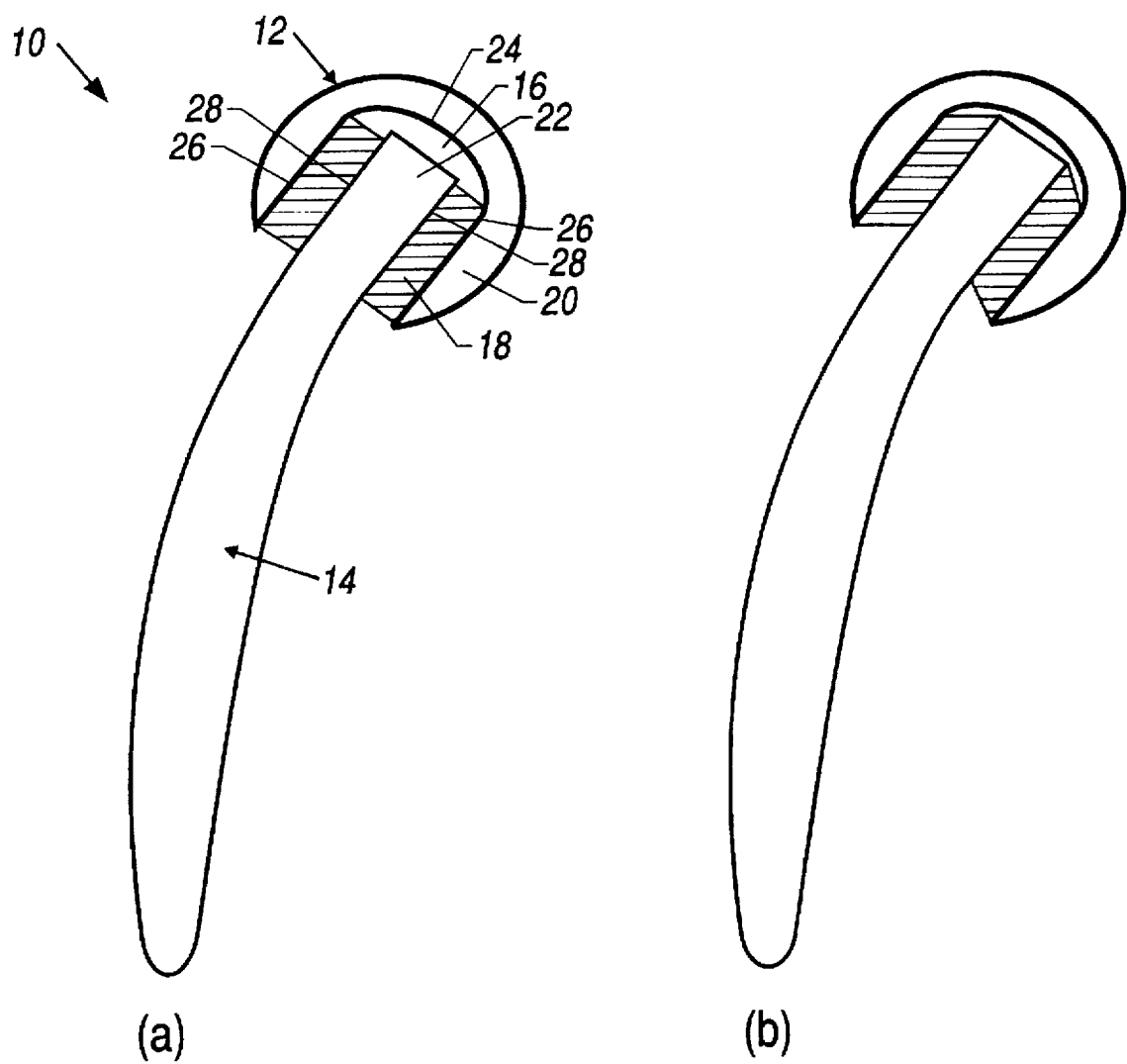
FIGS. 1a and 1b are a perspective view of one embodiment of the present invention in which the femoral head is split into at least two sections with elastomeric layer(s) attached between the stem and the head.

The invention will be described with reference to several embodiments, illustrated in the drawings, with like numerals being used to designate like parts. The invention also will be described with specific reference to a femoral head prosthesis; however, the present invention may be used to reduce stress levels in other load bearing prostheses as well. The present invention is particularly useful for prostheses designed to replace skeletal members.

FIG. 1 illustrates a femoral head prosthesis made according to the present invention. The femoral head prosthesis is labelled generally as 10. As already discussed, current hip replacement prostheses use a femoral head which is a one-piece component having a continuous head and stem. In contrast, a femoral head prosthesis made according to the present invention has several components—a separate head 12, a separate stem 14, and an elastomeric component 18, which will be discussed more fully below (FIG. 1).

The head 12 shown in the Figures should be distinguished from the acetabulum, which typically is a separate component of current hip replacement prostheses. Of course, the head 12 of the prosthesis described herein eventually should be movably engageable with an acetabulum; however, engagement between the femoral head and the acetabulum is not the subject matter of the present invention.

In FIG. 1, the separate head 12 and stem 14 of the femoral head prosthesis are mechanically connected by an elastomeric component 18. The elastomeric component 18 provides for passive shock absorption by permitting relative motion between the head 12 and the stem 14 of the prosthesis. In order for shock absorption to occur as a result of such relative motion, the elastomeric component 18 must be capable of either: (1) shear deformation, alone; (2) both shear and compressive deformation; or, (3) compressive deformation, alone.

FIG. 1 represents an embodiment in which the elastomeric component is capable primarily of shear deformation. The principles applied in the Figures are fully explained in the following references, all of which are incorporated herein by reference: E. F. Göbel, *Rubber Springs Design*, translated and edited by A. M. Brichta, John Wiley & Sons, New York, 1974; R. H. Finney and B. P. Gupta, "Design of Elastomeric Components by Using the Finite Element Technique," from *The Shock and Vibration Bulletin, Part 1. Opening Session, Panel Session, Shock Analysis, Shock Testing, Isolation and Damping*. September 1977, a publication of the Shock and Vibration Information Center, Naval Research Laboratory, Washington, D.C., Bulletin 47 (Part 1 of 4 parts), pp. 177–188; P. B. Lindley, *Eng'g Design with Natural Rubber*, NR Technical Bulletin, The Natural Rubber Producers Research Ass'n, London, 1964. With the foregoing design tools and the following teachings, a person of skill in the art should be able to design a prosthesis with a range of stiffness and damping properties to fit any particular design condition.

In FIG. 1, the spherical head 12 is split in half in order to show that the head 12 is hollow, forming a cavity 16. In the embodiment of FIG. 1, the cavity 16 is substantially "U"-shaped and has an inner surface 24 near the top of the head. The surface 24 is rounded and the sides 26 of the inner surface are substantially parallel to one another. The legs at the open end of the "U" form a shoulder at the distal end of the head. One end 22 of the stem 14 extends into the cavity 16, and the sides 28 of the stem end 22 preferably are substantially parallel to the respective sides 26 of the cavity 16.

Both the head 12 and the stem 14 may be made of substantially any of the biocompatible materials typically used for such components, a preferred material being titanium. In a preferred embodiment, the surface of the stem 14 has been primed to encourage tissue ingrowth, e.g., by applying a porous ceramic or porous titanium coating to the stem or by sandblasting. The head 12 preferably should have a smooth finish, except for the surface of the head onto which the elastomer is bonded. The elastomer bonding surface preferably should be treated, e.g., chemically or by sandblasting, to provide a greater surface area for bonding. The stem 14 is formed in the general shape of the medullary canal, and should be of sufficient length to extend a substantial distance into the medullary canal of the femur to be treated.

The elastomeric component 18 may be affixed to the surfaces 28 and 26 using a suitable biocompatible adhesive. In a preferred embodiment, the stem and head are sprayed with an adhesive, such as CHEMLOCK 608, available from Lord Corporation, Erie, Pa. The stem and head then may be placed into a mold and hot, uncured elastomer may be injected into a suitable cavity appropriately positioned adjacent to the surfaces 28 and 26. Since the adhesive is activated by heat, adherence, and curing of the hot elastomer will occur simultaneously. Alternately, the elastomeric component 18 may be formed separately and subsequently bonded to the surfaces 28 and 26. The surfaces 28 and 26 should be coated with adhesive, the pre-formed elastomeric component 18 should be appropriately placed, and heat should be applied to activate the adhesive.

In the embodiment shown in FIG. 1, a portion of the cavity 16 near the inner surface 24 at the top of the head is "empty" so that, when the stem 14 receives an impact, the elastomeric component 18 deforms (FIG. 1b) and the stem can move toward the upper inner surface 24 of the cavity 16.

The mechanical response of the elastomeric component 18 can be varied by material variations, such as varying the chemical nature of the elastomer, the stiffness of the elastomer, and the damping properties of the elastomer. The stiffness and the damping properties of the elastomer are related to the chemical type of elastomer and to its molecular properties and compounding ingredients. Methods of material property variation of elastomers are well known. The damping properties and attenuation properties of such elements are discussed by J. C. Snowdon, *Vibration and Shock in Damped Mechanical Systems*, John Wiley & Sons, New York (1968), incorporated herein by reference. In a preferred embodiment, the elastomeric component is an ethylene-propylene rubber. The mechanical response of the elastomeric component 18 also can be varied by modifying its physical dimensions; for example, thickening the elastomeric component 18 perpendicular to the load trajectory will render the assembly less stiff and more flexible.

Figure 2:
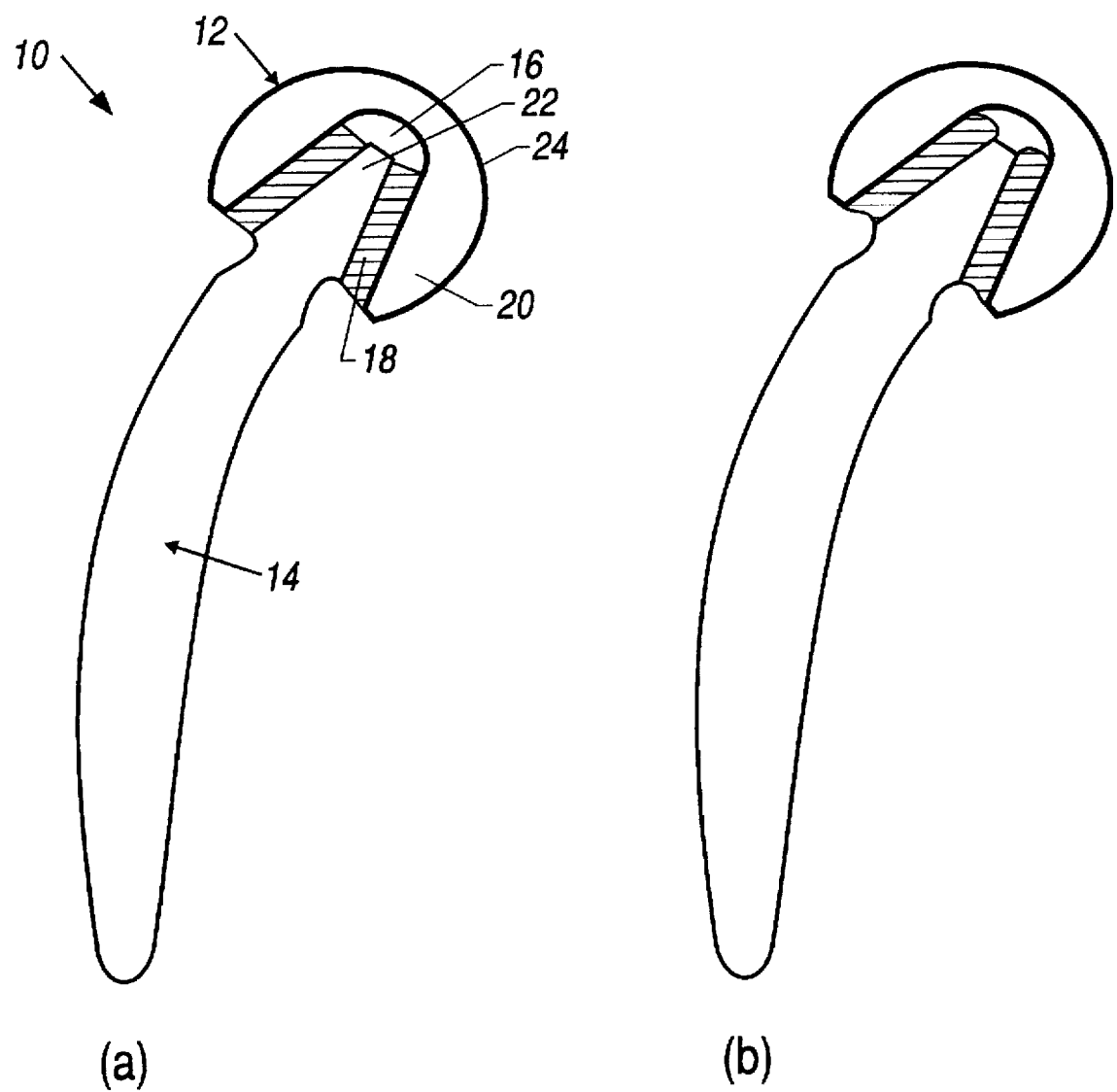
FIGS. 2a and 2b are a similar perspective view of a second embodiment of the present invention.

The embodiment shown in FIG. 2 is designed to provide shock absorption using both shear and compressive deformation. The prosthesis in FIG. 2 has a stem 14 which is similar to the stem in FIG. 1 except that the end 22 of the stem 14 is substantially conical; the cavity 16 inside of the head 12 is substantially conical, and the elastomeric component 18 that circumscribes the end 22 also is substantially conical. As a result, when an impact is transmitted to the stem 14 and then to the elastomeric component 18, shock absorption occurs due to both shear and compressive deformation of the elastomeric component 18 (FIG. 2b).

Figure 3:
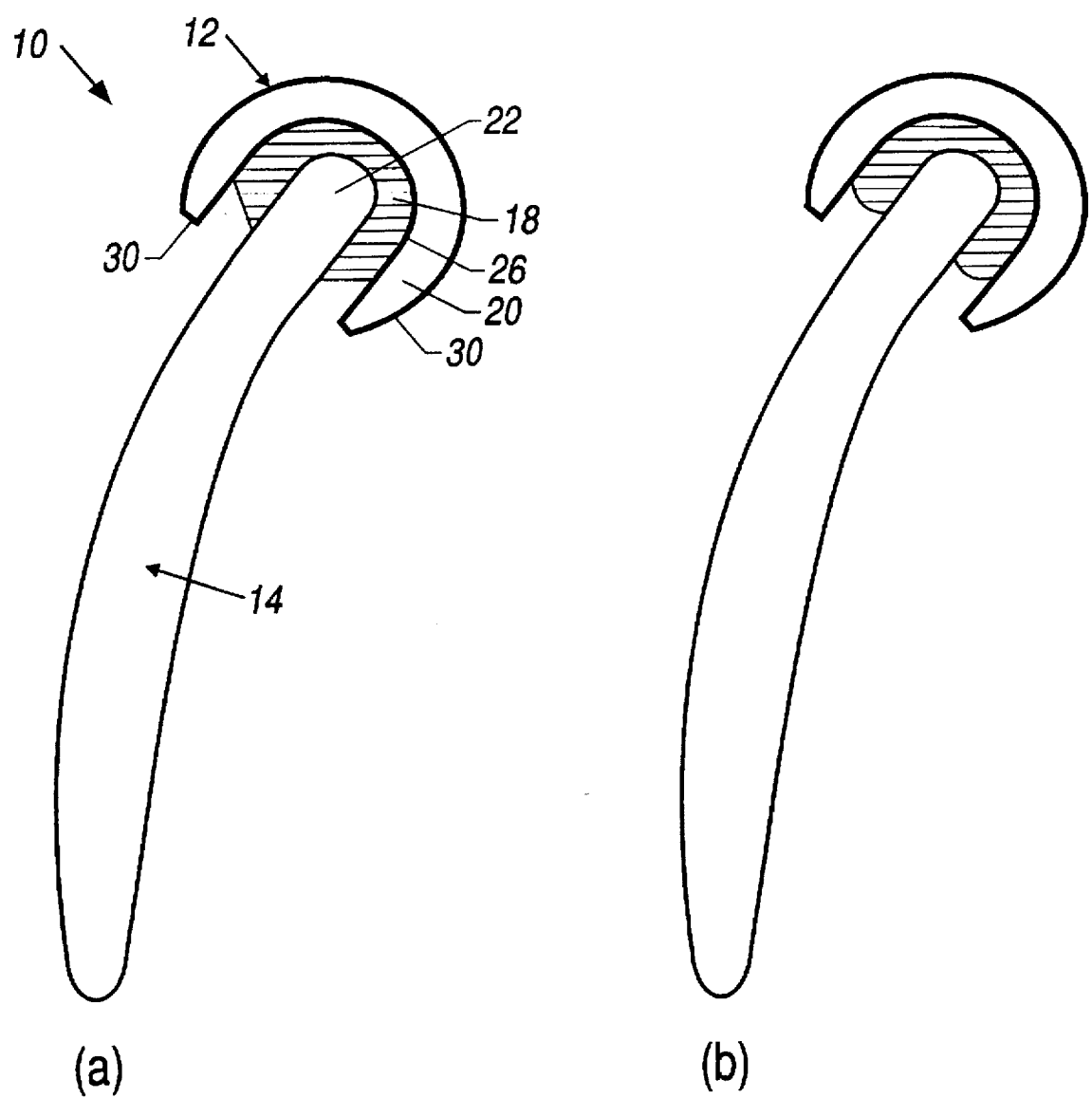
FIGS. 3a and 3b are a similar perspective view of a third embodiment of the present invention.

The embodiment in FIG. 3 shows a geometric configuration in which shock absorption takes place primarily by compressive deformation, alone. In FIG. 3, the hollow head 12 forms a substantially concave, C-shaped cavity 16, and the end 22 of the stem 14 is rounded. When the end 22 is inside of the head 12, the inside wall 26 of the head 12 and the outside wall of the end 22 are substantially concentric or "parallel." For present purposes, the term "parallel" is defined to include this substantially concentric configuration. In this embodiment, the elastomeric component 18 circumscribes a majority of the end 22 inside of the head 12 with the exception of a small portion near the open ends 30 of the "C." The amount of clearance required at the open ends 30 of the "C" will depend upon the amount of stiffness required in the prosthesis. The stiffness, deformation properties, and shock absorbing properties of the elastomeric component may be determined by an analysis method such as finite element stress and deformation analysis. This method is used in R. H. Finney and B. P. Gupta, "Design of Elastomeric Components by Using the Finite Element Technique," from *The Shock and Vibration Bulletin, Part 1. Opening Session, Panel Session, Shock Analysis, Shock Testing, Isolation and Damping*. September 1977, a publication of the Shock and Vibration Information Center, Naval Research Laboratory, Washington, D.C., Bulletin 47 (Part 1 of 4 parts), pp. 177–188, incorporated herein by reference.

In order for the elastomeric component 18 of FIG. 3 to absorb shock by substantially compressive deformation, the elastomeric component 18 must be deformable. In order to be deformable, the elastomeric component 18 must have a relatively low shear modulus, preferably a modulus of about $2.76 \times 10^7$ Pascal (4000 psi) or less. When the stem 14 of the embodiment in FIG. 3 is impacted, the force will be transmitted to the elastomeric component 18, and the elastomeric component 18 will absorb at least a portion of the shock by compressive deformation, as shown in FIG. 3.

A person of skill in the art will recognize that many modifications may be made to the present invention without departing from the spirit and scope of the present invention. The embodiment described herein is meant to be illustrative only and should not be taken as limiting the invention, which is defined in the following claims.

I claim:

1. A femoral head prosthesis capable of passive shock absorption comprising:

a head having an outer surface and an inner surface, said outer surface being movably engageable within an inner cavity of an acetabulum;

a separate stem having two ends, a first end adapted to be inserted into a medullary canal of a femur and a second end having an end surface and a periphery, aid end surface being substantially exposed and said periphery being in mechanical communication with said inner surface of said head via an elastomeric component that allows relative movement between said head and said stem, said elastomeric component being sufficiently deformable to provide passive shock absorption.

2. The prosthesis of claim 1 wherein said mechanical communication permits shear deformation of said elastomeric element.

3. The prosthesis of claim 1 wherein said mechanical communication permits both shear deformation and compressive deformation of said elastomeric element.

4. The prosthesis of claim 1 wherein said mechanical communication permits compressive deformation of said elastomeric element.

5. The prosthesis of claim 1 wherein said prosthesis is designed to replace a skeletal member and said elastomeric component has a shear modulus of $2.76 \times 10^7$ Pascal (4000 psi) or less.

6. The prosthesis of claim 2 wherein said prosthesis is designed to replace a skeletal member and said elastomeric component has a shear modulus of $2.76 \times 10^7$ Pascal (4000 psi) or less.

7. The prosthesis of claim 3 wherein said prosthesis is designed to replace a skeletal member and said elastomeric component has a shear modulus of $2.76 \times 10^7$ Pascal (4000 psi) or less.

8. The prosthesis of claim 1 wherein a majority of said surfaces in mechanical communication are substantially parallel.

9. The prosthesis of claim 8 further comprising a cavity between said inner surface of said head and outer surface of said second end to prevent contact between said surfaces when said elastomeric component is deformed.

10. The prosthesis of claim 1 wherein said second end is substantially cylindrical and has a top surface and an outer spherical surface;

said inner surface of said cavity is substantially parallel to said outer spherical surface of said second end; and said cavity is adjacent to said top surface of said second end.

* * * * *